(12) United States Patent
Culbertson et al.

(10) Patent No.: US 10,709,548 B2
(45) Date of Patent: Jul. 14, 2020

(54) METHOD AND APPARATUS FOR CREATING OCULAR SURGICAL AND RELAXING INCISIONS

(71) Applicant: AMO Development, LLC, Santa Ana, CA (US)

(72) Inventors: William Culbertson, Miami, CA (US); David Angeley, Charlottesville, VA (US); George Marcellino, Santa Cruz, CA (US); Dan E. Andersen, Menlo Park, CA (US)

(73) Assignee: AMO Development, LLC, Santa Ana, CA (US)

( * ) Notice: Subject to any disclaimer, the term of this patent is extended or adjusted under 35 U.S.C. 154(b) by 0 days.

(21) Appl. No.: 14/668,696

(22) Filed: Mar. 25, 2015

(65) Prior Publication Data
US 2015/0196429 A1    Jul. 16, 2015

Related U.S. Application Data

(62) Division of application No. 13/569,103, filed on Aug. 7, 2012, now Pat. No. 9,233,024, which is a division
(Continued)

(51) Int. Cl.
*A61F 2/16* (2006.01)
*A61F 9/00* (2006.01)
(Continued)

(52) U.S. Cl.
CPC .............. *A61F 2/1613* (2013.01); *A61F 2/16* (2013.01); *A61F 2/1637* (2013.01);
(Continued)

(58) Field of Classification Search
CPC .......... A61F 9/008; A61F 2/1613; A61F 2/16; A61F 2/1637; A61F 2/1648;
(Continued)

(56) References Cited

U.S. PATENT DOCUMENTS

| 4,169,664 A | 10/1979 | Bailey, Jr. |
| 4,309,998 A | 1/1982 | Aron et al. |

(Continued)

FOREIGN PATENT DOCUMENTS

| DE | 19938203 A1 | 2/2001 |
| DE | 10207535 A1 | 9/2003 |

(Continued)

OTHER PUBLICATIONS

Abstract of AU Publication No. 2007292491, Publication Date Mar. 13, 2008, which is the AU counterpart of the WO08030718 A2 application.
(Continued)

*Primary Examiner* — Lynsey C Eiseman
*Assistant Examiner* — Jessandra F Hough
(74) *Attorney, Agent, or Firm* — Johnson & Johnson Surgical Vision, Inc.

(57) ABSTRACT

A scanning system for treating target tissue in a patient's eye includes an ultrafast laser source configured to deliver a laser beam comprising a plurality of laser pulses; an Optical Coherence Tomography (OCT) device configured to generate signals which may be used to create an image of the cornea and limbus of the eye of the patient; a scanner configured to focus and direct the laser beam in a pattern within the cornea or limbus to create incisions therein; and a controller operatively coupled to the laser source and scanner configured to control the scanner to adjust the position of the laser beam based upon the signals from the OCT device to create a cataract incision in the cornea or limbus that provides access for lens removal instrumentation to a crystalline lens of the patient's eye, and a relaxation incision in the cornea or limbus.

17 Claims, 6 Drawing Sheets

Related U.S. Application Data of application No. 12/048,186, filed on Mar. 13, 2008, now Pat. No. 9,233,023.

(60) Provisional application No. 60/906,944, filed on Mar. 13, 2007.

(51) Int. Cl.
*A61F 9/007* (2006.01)
*A61F 9/008* (2006.01)
*A61F 9/009* (2006.01)

(52) U.S. Cl.
CPC .......... *A61F 2/1648* (2013.01); *A61F 2/1662* (2013.01); *A61F 9/00* (2013.01); *A61F 9/008* (2013.01); *A61F 9/009* (2013.01); *A61F 9/00754* (2013.01); *A61F 9/00812* (2013.01); *A61F 9/00825* (2013.01); *A61F 2002/1683* (2013.01); *A61F 2002/16901* (2015.04); *A61F 2009/0087* (2013.01); *A61F 2009/0088* (2013.01); *A61F 2009/00859* (2013.01); *A61F 2009/00872* (2013.01); *A61F 2009/00887* (2013.01); *A61F 2009/00897* (2013.01); *A61F 2220/0016* (2013.01)

(58) Field of Classification Search
CPC .......... A61F 9/00825; A61F 2002/1683; A61F 2009/00859; A61F 2009/0087; A61F 2009/00872; A61F 2009/0088; A61F 2009/00887; A61F 2009/00897; A61F 9/00; A61F 9/0825; A61F 2220/0016; A61F 9/00754; A61F 9/009; A61F 2/1662
See application file for complete search history.

(56) References Cited

U.S. PATENT DOCUMENTS

| | | | |
|---|---|---|---|
| 4,538,608 A | 9/1985 | L'Esperance, Jr. | |
| 4,684,796 A | 8/1987 | Johnson | |
| 4,901,718 A | 2/1990 | Bille et al. | |
| 4,907,586 A | 3/1990 | Bille et al. | |
| 4,917,486 A | 4/1990 | Raven et al. | |
| 4,995,715 A | 2/1991 | Cohen | |
| 5,098,426 A | 3/1992 | Sklar et al. | |
| 5,112,328 A | 5/1992 | Taboada et al. | |
| 5,246,435 A | 9/1993 | Bille et al. | |
| 5,257,988 A | 11/1993 | L'Esperance, Jr. | |
| 5,284,477 A | 2/1994 | Hanna et al. | |
| 5,336,216 A | 8/1994 | Dewey | |
| 5,336,217 A | 8/1994 | Buys et al. | |
| 5,391,165 A | 2/1995 | Fountain et al. | |
| 5,411,510 A * | 5/1995 | Fugo .................. | A61B 17/3211 128/898 |
| 5,437,658 A | 8/1995 | Muller et al. | |
| 5,459,570 A | 10/1995 | Swanson et al. | |
| 5,480,396 A | 1/1996 | Simon et al. | |
| 5,493,109 A | 2/1996 | Wei et al. | |
| 5,505,693 A | 4/1996 | Mackool | |
| 5,520,679 A | 5/1996 | Lin | |
| 5,531,753 A | 7/1996 | Oliveira | |
| 5,549,632 A | 8/1996 | Lai | |
| 5,599,341 A | 2/1997 | Mathis et al. | |
| 5,702,441 A | 12/1997 | Zhou | |
| 5,719,673 A | 2/1998 | Dorsel et al. | |
| 5,720,894 A | 2/1998 | Neev et al. | |
| 5,722,427 A | 3/1998 | Wakil et al. | |
| 5,743,902 A | 4/1998 | Trost | |
| 5,748,352 A | 5/1998 | Hattori | |
| 5,748,898 A | 5/1998 | Ueda | |
| 5,779,696 A | 7/1998 | Berry et al. | |
| 5,865,830 A | 2/1999 | Parel et al. | |
| 5,906,611 A | 5/1999 | Dodick et al. | |
| 5,957,915 A | 9/1999 | Trost | |
| 5,971,978 A | 10/1999 | Mukai | |
| 5,980,513 A | 11/1999 | Frey et al. | |
| 5,984,916 A | 11/1999 | Lai | |
| 5,993,438 A | 11/1999 | Juhasz et al. | |
| 6,002,127 A | 12/1999 | Vestal et al. | |
| 6,004,314 A * | 12/1999 | Wei .................. | A61B 3/102 606/12 |
| 6,019,472 A | 2/2000 | Koester et al. | |
| 6,053,613 A | 4/2000 | Wei et al. | |
| 6,057,543 A | 5/2000 | Vestal et al. | |
| 6,079,417 A | 6/2000 | Fugo | |
| 6,099,522 A * | 8/2000 | Knopp .................. | B23K 26/04 606/10 |
| 6,110,166 A | 8/2000 | Juhasz | |
| 6,111,645 A | 8/2000 | Tearney et al. | |
| 6,146,375 A | 11/2000 | Juhasz et al. | |
| 6,149,644 A | 11/2000 | Xie | |
| 6,171,336 B1 | 1/2001 | Sawusch | |
| 6,210,401 B1 | 4/2001 | Lai | |
| 6,254,595 B1 | 7/2001 | Juhasz et al. | |
| 6,281,493 B1 | 8/2001 | Vestal et al. | |
| 6,322,556 B1 | 11/2001 | Gwon et al. | |
| 6,324,191 B1 | 11/2001 | Horvath | |
| 6,325,792 B1 | 12/2001 | Swinger et al. | |
| 6,328,733 B1 | 12/2001 | Trost | |
| RE37,504 E | 1/2002 | Lin | |
| 6,344,040 B1 | 2/2002 | Juhasz et al. | |
| RE37,585 E | 3/2002 | Mourou et al. | |
| 6,373,571 B1 | 4/2002 | Juhasz et al. | |
| 6,396,587 B1 | 5/2002 | Knupfer et al. | |
| D459,806 S | 7/2002 | Webb | |
| D459,807 S | 7/2002 | Webb | |
| D462,442 S | 9/2002 | Webb | |
| D462,443 S | 9/2002 | Webb | |
| 6,454,761 B1 | 9/2002 | Freedman | |
| 6,497,701 B2 | 12/2002 | Shimmick et al. | |
| 6,585,723 B1 * | 7/2003 | Sumiya .................. | A61B 3/107 606/10 |
| 6,610,050 B2 | 8/2003 | Bille | |
| 6,623,476 B2 | 9/2003 | Kurtz et al. | |
| 6,638,271 B2 | 10/2003 | Munnerlyn et al. | |
| 6,648,877 B1 | 11/2003 | Juhasz et al. | |
| 6,652,511 B1 | 11/2003 | Tomita | |
| 6,676,653 B2 | 1/2004 | Juhasz et al. | |
| 6,693,927 B1 | 2/2004 | Horvath et al. | |
| 6,706,036 B2 | 3/2004 | Lai | |
| 6,751,033 B2 | 6/2004 | Goldstein et al. | |
| 6,902,561 B2 | 6/2005 | Kurtz et al. | |
| 7,027,233 B2 | 4/2006 | Goldstein et al. | |
| 7,146,983 B1 | 12/2006 | Hohla et al. | |
| 7,655,002 B2 | 2/2010 | Myers I et al. | |
| 7,717,907 B2 | 5/2010 | Ruiz et al. | |
| 8,186,357 B2 | 5/2012 | Lubatschowski et al. | |
| 8,262,646 B2 | 9/2012 | Frey et al. | |
| 8,350,183 B2 | 1/2013 | Vogel et al. | |
| 8,382,745 B2 | 2/2013 | Naranjo-Tackman et al. | |
| 8,394,084 B2 | 3/2013 | Blumenkranz et al. | |
| 8,414,564 B2 | 4/2013 | Goldshleger et al. | |
| 8,430,921 B2 | 4/2013 | Wong et al. | |
| 8,808,279 B2 | 8/2014 | Muhlhoff et al. | |
| 9,107,732 B2 | 8/2015 | Blumenkranz et al. | |
| 9,271,870 B2 | 3/2016 | Palanker et al. | |
| 9,474,648 B2 | 10/2016 | Palanker et al. | |
| 9,474,649 B2 | 10/2016 | Palanker et al. | |
| 9,480,601 B2 | 11/2016 | Palanker et al. | |
| 2001/0016736 A1 | 8/2001 | Lin | |
| 2001/0020163 A1 | 9/2001 | Clapman et al. | |
| 2002/0103478 A1 | 8/2002 | Gwon et al. | |
| 2002/0128637 A1 | 9/2002 | Von et al. | |
| 2002/0173778 A1 | 11/2002 | Knopp et al. | |
| 2003/0053219 A1 | 3/2003 | Manzi | |
| 2003/0060880 A1 | 3/2003 | Feingold | |
| 2003/0098834 A1 | 5/2003 | Ide et al. | |
| 2003/0125718 A1 | 7/2003 | Munnerlyn et al. | |
| 2004/0021874 A1 | 2/2004 | Shimmick | |
| 2004/0054358 A1 | 3/2004 | Cox | |
| 2004/0148022 A1 | 7/2004 | Eggleston | |
| 2004/0199149 A1 * | 10/2004 | Myers .................. | A61F 9/008 606/4 |

(56) References Cited

U.S. PATENT DOCUMENTS

| | | |
|---|---|---|
| 2004/0199150 A1 | 10/2004 | Lai |
| 2004/0243112 A1* | 12/2004 | Bendett .............. A61F 9/00827 606/5 |
| 2004/0263785 A1* | 12/2004 | Chernyak ............ A61B 3/1015 351/246 |
| 2005/0096639 A1 | 5/2005 | Slatkine et al. |
| 2005/0241653 A1* | 11/2005 | Van Heugten .......... A61F 9/007 128/898 |
| 2006/0100677 A1 | 5/2006 | Blumenkranz et al. |
| 2006/0106372 A1 | 5/2006 | Kuhn et al. |
| 2006/0195076 A1 | 8/2006 | Blumenkranz et al. |
| 2006/0224147 A1 | 10/2006 | Abe et al. |
| 2006/0235428 A1 | 10/2006 | Silvestrini |
| 2006/0247659 A1* | 11/2006 | Moeller ................ A61B 3/107 606/107 |
| 2006/0279698 A1 | 12/2006 | Muehlhoff et al. |
| 2007/0173794 A1 | 7/2007 | Frey et al. |
| 2007/0173795 A1 | 7/2007 | Frey et al. |
| 2007/0185175 A1 | 8/2007 | Liu et al. |
| 2007/0276269 A1* | 11/2007 | Yun ....................... A61B 3/102 600/504 |
| 2007/0282313 A1 | 12/2007 | Huang et al. |
| 2008/0033406 A1 | 2/2008 | Andersen et al. |
| 2008/0058704 A1* | 3/2008 | Hee ....................... A61F 9/0017 604/21 |
| 2008/0058841 A1 | 3/2008 | Kurtz et al. |
| 2008/0082086 A1* | 4/2008 | Kurtz ..................... A61F 2/142 606/4 |
| 2008/0177256 A1 | 7/2008 | Loesel et al. |
| 2008/0281303 A1 | 11/2008 | Culbertson et al. |
| 2008/0281413 A1 | 11/2008 | Culbertson et al. |
| 2009/0012507 A1 | 1/2009 | Culbertson et al. |
| 2009/0118718 A1* | 5/2009 | Raksi ..................... A61F 9/008 606/5 |
| 2009/0131921 A1 | 5/2009 | Kurtz et al. |
| 2010/0137850 A1 | 6/2010 | Culbertson et al. |
| 2010/0137982 A1 | 6/2010 | Culbertson et al. |
| 2010/0137983 A1 | 6/2010 | Culbertson et al. |
| 2010/0191226 A1 | 7/2010 | Blumenkranz et al. |
| 2011/0184392 A1 | 7/2011 | Culbertson et al. |
| 2011/0319873 A1 | 12/2011 | Raksi et al. |
| 2011/0319875 A1 | 12/2011 | Loesel et al. |

FOREIGN PATENT DOCUMENTS

| | | |
|---|---|---|
| DE | 10334108 A1 | 2/2005 |
| DE | 10339520 A1 | 3/2005 |
| DE | 102005027355 A1 | 12/2006 |
| EP | 1279386 A1 | 1/2003 |
| EP | 0700310 B1 | 11/2003 |
| EP | 1364632 A1 | 11/2003 |
| EP | 2211802 B1 | 6/2012 |
| JP | 2006136714 A | 6/2006 |
| RU | 2165248 C2 | 4/2001 |
| WO | 9009141 A2 | 8/1990 |
| WO | 9308877 A1 | 5/1993 |
| WO | 9407424 A1 | 4/1994 |
| WO | 0119303 A1 | 3/2001 |
| WO | 02064031 A2 | 8/2002 |
| WO | 2004026198 A2 | 4/2004 |
| WO | 2004026198 A3 | 11/2004 |
| WO | 2005102200 A2 | 11/2005 |
| WO | 2006074469 A2 | 7/2006 |
| WO | 2006119584 A1 | 11/2006 |
| WO | 2008030718 A2 | 3/2008 |
| WO | 2009059251 A2 | 5/2009 |

OTHER PUBLICATIONS

Baikoff G., et al., "Contact Between 3 Phakic Intraocular Lens Models and the Crystalline Lens: An Anterior Chamber Optical Coherence Tomography Study," Journal of Cataract and Refractive Surgery, 2004, vol. 30 (9), pp. 2007-2012.

Boppart S.A., et al., "High-Resolution Optical Coherence Tomography-Guided Laser Ablation of Surgical Tissue," Journal of Surgical Research, 1999, vol. 82 (2), pp. 275-284.

Dodick J.M., et al., "Current Techniques in Laser Cataract Surgery," in: Phacoemulsification: New Technology and Clinical Application, Fine H.I., ed., Slack Incorporated, Chapter 9, 1996, 17 pages.

European Search Report for Application No. EP13173305, dated Oct. 17, 2013, 7 pages.

European Search Report for Application No. EP13173306, dated Sep. 18, 2013, 6 pages.

Extended European Search Report for Application No. EP14166814, dated Oct. 10, 2014, 6 pages.

Extended European Search Report for Application No. EP14166815, dated Oct. 10, 2014, 6 pages.

Fujimoto J.G., et al., "Optical and Acoustical Imaging of Biological Media: Optical Coherence Tomography," Applied Physics and Biophysics, 2001, vol. 2 (IV), pp. 1099-1111.

Geerling G., et al., "Initial Clinical Experience with the Picosecond Nd:YLF Laser for Intraocular Therapeutic Applications," British Journal of Ophthalmology, 1998, vol. 82 (5), pp. 504-509.

Gimbel H.V., et al., "Continuous Curvilinear Capsulorhexis," Journal of Cataract and Refractive Surgery, 1991, vol. 17 (1), pp. 110-111.

Gimbel H.V., et al., "Development, Advantages and Methods of the Continuous Circular Capsulorhexis Technique," Journal of Cataract and Refractive Surgery, 1990, vol. 16 (1), pp. 31-37.

Gimbel H.V., et al., "Principles of Nuclear Phaco Emulsification"In: Cataract Surgery Techniques Complications and Management, 2nd edition., Steinert et al., 2004, Chap. 15, pp. 153-181.

International Search Report and Written Opinion for Application No. PCT/US08/03382, dated Jul. 25, 2008, 5 pages.

Izatt J.A., et al., "Micrometer-Scale Resolution Imaging of the Anterior Eye In Vivo With Optical Coherence Tomography," Arch Ophthalmology, 1994, vol. 112 (12), pp. 1584-1589.

Masket S., "Control of Corneal Astigmatism in regard to Multifocal Lens Implants," in: Current Concepts of Multifocal Intraocular Lenses, Maxwell A., eds., Slack Incorporated, 1991, Chapter 15, 22 pages.

Notification of Reason for Rejection dated Sep. 17, 2014 for Japanese Application No. 2013228661 filed Nov. 1, 2011.

Steinert et al., "Neodymium: Yttrium-Aluminum-Garnet Laser Posterior Capsulotomy"In: Cataract Surgery Techniques Complications and Management, 2nd edition., Steinert et al., 2004, Chap. 44, pp. 531-544.

Supplementary European Search Report for Application No. EP08726822, dated Apr. 9, 2010, 6 pages.

* cited by examiner

US 10,709,548 B2

METHOD AND APPARATUS FOR CREATING OCULAR SURGICAL AND RELAXING INCISIONS

CROSS-REFERENCE TO RELATED APPLICATIONS

This application is a divisional of U.S. patent application Ser. No. 13/569,103, filed Aug. 7, 2012, which is a divisional of U.S. patent application Ser. No. 12/048,186, filed Mar. 13, 2008, which claims the benefit under 35 USC § 119 of U.S. Provisional Application No. 60/906,944, filed Mar. 13, 2007, now expired, which is incorporated by reference as if set forth fully herein.

FIELD OF THE INVENTION

The present invention relates to ophthalmic surgical procedures and systems.

BACKGROUND OF THE INVENTION

Cataract extraction is one of the most commonly performed surgical procedures in the world with estimated 2.5 million cases performed annually in the United States and 9.1 million cases worldwide in 2000. This was expected to increase to approximately 13.3 million estimated global cases in 2006. This market is composed of various segments including intraocular lenses for implantation, viscoelastic polymers to facilitate surgical maneuvers, disposable instrumentation including ultrasonic phacoemulsification tips, tubing, and various knives and forceps. Modem cataract surgery is typically performed using a technique termed phacoemulsification in which an ultrasonic tip with an associated water stream for cooling purposes is used to sculpt the relatively hard nucleus of the lens after performance of an opening in the anterior lens capsule termed anterior capsulotomy or more recently capsulorhexis. Following these steps as well as removal of residual softer lens cortex by aspiration methods without fragmentation, a synthetic foldable intraocular lens (IOLs) is inserted into the eye through a small incision.

Many cataract patients are astigmatic. Astigmatism can occur when the cornea has a different curvature one direction than the other. IOLs are not presently used to correct beyond 5 D of astigmatism, even though many patients have more severe aberrations. Correcting it further often involves making the corneal shape more spherical, or at least more radially symmetrical. There have been numerous approaches, including Corneaplasty, Astigmatic Keratotomy (AK), Corneal Relaxing Incisions (CRI), and Limbal Relaxing Incisions (LRI). All are done using manual, mechanical incisions. Presently, astigmatism cannot easily or predictably be corrected fully using standard techniques and approaches. About one third of those who have surgery to correct the irregularity find that their eyes regress to a considerable degree and only a small improvement is noted. Another third of the patients find that the astigmatism has been significantly reduced but not fully corrected. The remaining third have the most encouraging results with most or all of the desired correction achieved.

What is needed are ophthalmic methods, techniques and apparatus to advance the standard of care of corneal shaping that may be associated with invasive cataract and other ophthalmic pathologies.

SUMMARY OF THE INVENTION

Rapid and precise opening formation in the cornea and/or limbus are possible using a scanning system that implements patterned laser cutting. The patterned laser cutting improves accuracy and precision, while decreasing procedure time.

A scanning system for treating target tissue in a patient's eye includes a light source for generating a light beam, a scanner for deflecting the light beam to form first and second treatment patterns of the light beam under the control of a controller, and a delivery system for delivering the first treatment pattern to the target tissue to form a cataract incision therein that provides access to an eye chamber of the patient's eye. The delivery system is also for delivering the second treatment pattern to the target tissue to form a relaxation incision along or near limbus tissue or along corneal tissue anterior to the limbus tissue of the patient's eye to reduce astigmatism thereof.

A method of treating target tissue in a patient's eye includes generating a light beam, deflecting the light beam using a scanner to form first and second treatment patterns, delivering the first treatment pattern to the target tissue to form an incision that provides access to an eye chamber of the patient's eye, and delivering the second treatment pattern to the target tissue to form a relaxation incision along or near limbus tissue or along corneal tissue anterior to the limbus tissue of the patient's eye to reduce astigmatism thereof.

Other objects and features of the present invention will become apparent by a review of the specification, claims and appended figures.

DETAILED DESCRIPTION OF THE PREFERRED EMBODIMENTS

Figure 1:
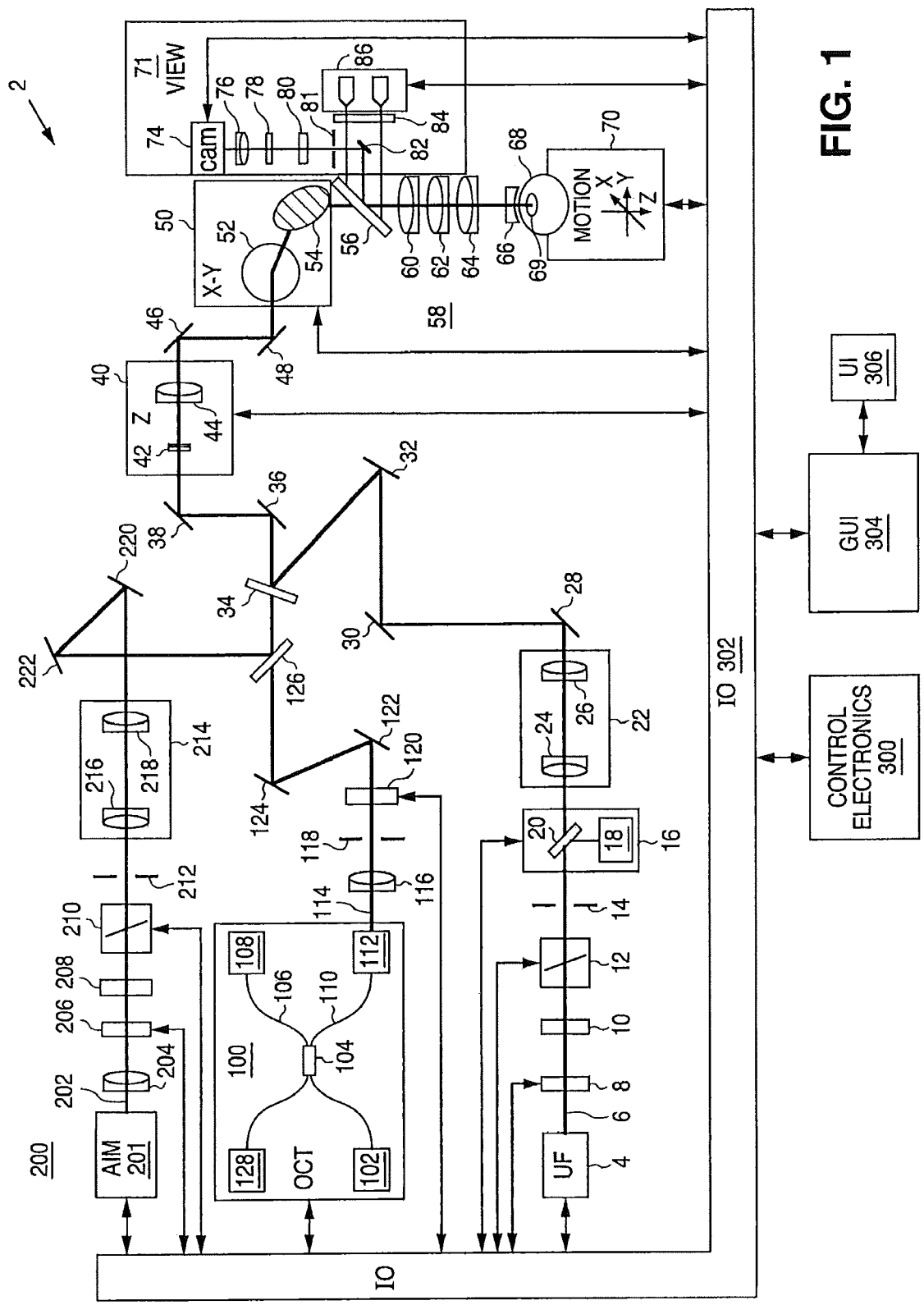
FIG. 1 is a schematic diagram of the optical beam scanning system.

The techniques and systems disclosed herein provide many advantages over the current standard of care. Specifically, rapid and precise openings in the cornea and/or limbus are formed using 3-dimensional patterned laser cutting. The accuracy and precision of the incisions are improved over traditional methods, while the duration of the procedure and the risk associated with creating incisions are both reduced. The present invention can utilize anatomical and optical characterization and feedback to perform astigmatic keratotomy such as limbal and corneal relaxing incisions in conjunction with the creation of surgical incision that provides the surgeon access to the anterior chamber of an eye. The surgical incision may be made completely, or partially, depending upon the clinical situation. A wavefront sensor, interferometer, surface profiler, or other such device may be used to yield prescriptions for correcting the astigmatism or other visual aberrations. Likewise, these same devices may be used to verify the surgical correction of the patterned scanning system, even adjusting it during the treatment procedure to produce the desired outcome. Furthermore, the present invention may be used in multiple sessions to coordinate the healing of the astigmatic correction, and drive the corrective treatment over the course of the wound healing process. The present invention also provides for the image guided alignment of the incision.

There are surgical approaches provided by the present invention that enable the formation of very small and geometrically precise opening(s) and incision(s) in precise locations in and around the cornea and limbus. The incisions enable greater precision or modifications to conventional ophthalmic procedures as well as enable new procedures. The incision is not limited only to circular shapes but may be any shape that is conducive to healing or follow on procedures. These incisions might be placed such that they are able to seal spontaneously; or with autologous or synthetic tissue glue, photochemical bonding agent, or other such method. Furthermore, the present invention provides for the automated generation of incision patterns for optimal effect.

Another procedure enabled by the techniques described herein provides for the controlled formation of an incision or pattern of incisions. Conventional techniques are confined to areas accessible from outside the eye using mechanical cutting instruments and thus can only create incisions from anterior to posterior segments of tissue. In contrast, the controllable, patterned laser techniques described herein may be used to create an incision in virtually any position and in virtually any shape. Matching incisions may be made in both the anterior and posterior sections. The present invention is uniquely suited to perform such matching incisions.

Furthermore, these incisions may be tailored to complement an asymmetric IOL that is being inserted as part of the procedure or has been previously inserted. The present invention enables the measurement of the IOL placement and subsequent automated calculation and generation of these complimentary corneal or limbus incisions. The controllable, patterned laser techniques described herein have available and/or utilize precise lens measurement and other dimensional information that allows the incision or opening formation while minimizing impact on surrounding tissue.

The present invention can be implemented by a system that projects or scans an optical beam into a patient's eye 68, such as system 2 shown in FIG. 1 which includes an ultrafast (UF) light source 4 (e.g. a femtosecond laser). Using this system, a beam may be scanned in a patient's eye in three dimensions: X, Y, Z. In this embodiment, the UF wavelength can vary between 1010 nm to 1100 nm and the pulse width can vary from 100 fs to 10000 fs. The pulse repetition frequency can also vary from 10 kHz to 250 kHz. Safety limits with regard to unintended damage to non-targeted tissue bound the upper limit with regard to repetition rate and pulse energy; while threshold energy, time to complete the procedure and stability bound the lower limit for pulse energy and repetition rate. The peak power of the focused spot in the eye 68 and specifically within the crystalline lens 69 and anterior capsule of the eye is sufficient to produce optical breakdown and initiate a plasma-mediated ablation process. Near-infrared wavelengths are preferred because linear optical absorption and scattering in biological tissue is reduced across that spectral range. As an example, laser 4 may be a repetitively pulsed 1035 nm device that produces 500 fs pulses at a repetition rate of 100 kHz and an individual pulse energy in the ten microjoule range.

The laser 4 is controlled by control electronics 300, via an input and output device 302, to create optical beam 6. Control electronics 300 may be a computer, microcontroller, etc. In this example, the entire system is controlled by the controller 300, and data moved through input/output device IO 302. A graphical user interface GUI 304 may be used to set system operating parameters, process user input (UI) 306 on the GUI 304, and display gathered information such as images of ocular structures.

The generated UF light beam 6 proceeds towards the patient eye 68 passing through half-wave plate, 8, and linear polarizer, 10. The polarization state of the beam can be adjusted so that the desired amount of light passes through half-wave plate 8 and linear polarizer 10, which together act as a variable attenuator for the UF beam 6. Additionally, the orientation of linear polarizer 10 determines the incident polarization state incident upon beam combiner 34, thereby optimizing beam combiner throughput.

The UF beam proceeds through a shutter 12, aperture 14, and a pickoff device 16. The system controlled shutter 12 ensures on/off control of the laser for procedural and safety reasons. The aperture sets an outer useful diameter for the laser beam and the pickoff monitors the output of the useful beam. The pickoff device 16 includes of a partially reflecting mirror 20 and a detector 18. Pulse energy, average power, or a combination may be measured using detector 18. The information can be used for feedback to the half-wave plate 8 for attenuation and to verify whether the shutter 12 is open or closed. In addition, the shutter 12 may have position sensors to provide a redundant state detection.

The beam passes through a beam conditioning stage 22, in which beam parameters such as beam diameter, divergence, circularity, and astigmatism can be modified. In this illustrative example, the beam conditioning stage 22 includes a 2 element beam expanding telescope comprised of spherical optics 24 and 26 in order to achieve the intended beam size and collimation. Although not illustrated here, an anamorphic or other optical system can be used to achieve the desired beam parameters. The factors used to determine these beam parameters include the output beam parameters of the laser, the overall magnification of the system, and the desired numerical aperture (NA) at the treatment location. In addition, the optical system 22 can be used to image aperture 14 to a desired location (e.g. the center location between the 2-axis scanning device 50 described below). In this way, the amount of light that makes it through the aperture 14 is assured to make it through the scanning system. Pickoff device 16 is then a reliable measure of the usable light.

After exiting conditioning stage 22, beam 6 reflects off of fold mirrors 28, 30, & 32. These mirrors can be adjustable for alignment purposes. The beam 6 is then incident upon beam combiner 34. Beam combiner 34 reflects the UF beam 6 (and transmits both the OCT 114 and aim 202 beams described below). For efficient beam combiner operation, the angle of incidence is preferably kept below 45 degrees and the polarization where possible of the beams is fixed. For the UF beam 6, the orientation of linear polarizer 10 provides fixed polarization.

Following the beam combiner 34, the beam 6 continues onto the z-adjust or Z scan device 40. In this illustrative example the z-adjust includes a Galilean telescope with two lens groups 42 and 44 (each lens group includes one or more lenses). Lens group 42 moves along the z-axis about the collimation position of the telescope. In this way, the focus position of the spot in the patient's eye 68 moves along the z-axis as indicated. In general there is a fixed linear relationship between the motion of lens 42 and the motion of the focus. In this case, the z-adjust telescope has an approximate 2.times.beam expansion ratio and a 1:1 relationship of the movement of lens 42 to the movement of the focus. Alternatively, lens group 44 could be moved along the z-axis to actuate the z-adjust, and scan. The z-adjust is the z-scan device for treatment in the eye 68. It can be controlled automatically and dynamically by the system and selected to be independent or to interplay with the X-Y scan device described next. Mirrors 36 and 38 can be used for aligning the optical axis with the axis of z-adjust device 40.

After passing through the z-adjust device 40, the beam 6 is directed to the x-y scan device by mirrors 46 & 48. Mirrors 46 & 48 can be adjustable for alignment purposes. X-Y scanning is achieved by the scanning device 50 preferably using two mirrors 52 & 54 under the control of control electronics 300, which rotate in orthogonal directions using motors, galvanometers, or any other well known optic moving device. Mirrors 52 & 54 are located near the telecentric position of the objective lens 58 and contact lens 66 combination described below. Tilting these mirrors 52/54 causes them to deflect beam 6, causing lateral displacements in the plane of UF focus located in the patient's eye 68. Objective lens 58 may be a complex multi-element lens element, as shown, and represented by lenses 60, 62, and 64. The complexity of the lens 58 will be dictated by the scan field size, the focused spot size, the available working distance on both the proximal and distal sides of objective 58, as well as the amount of aberration control. An f-theta lens 58 of focal length 60 mm generating a spot size of 10 .mu.m, over a field of 10 mm, with an input beam size of 15 mm diameter is an example. Alternatively, X-Y scanning by scanner 50 may be achieved by using one or more moveable optical elements (e.g. lenses, gratings) which also may be controlled by control electronics 300, via input and output device 302.

The aiming and treatment scan patterns can be automatically generated by the scanner 50 under the control of controller 300. Such patterns may be comprised of a single spot of light, multiple spots of light, a continuous pattern of light, multiple continuous patterns of light, and/or any combination of these. In addition, the aiming pattern (using aim beam 202 described below) need not be identical to the treatment pattern (using light beam 6), but preferably at least defines its boundaries in order to assure that the treatment light is delivered only within the desired target area for patient safety. This may be done, for example, by having the aiming pattern provide an outline of the intended treatment pattern. This way the spatial extent of the treatment pattern may be made known to the user, if not the exact locations of the individual spots themselves, and the scanning thus optimized for speed, efficiency and accuracy. The aiming pattern may also be made to be perceived as blinking in order to further enhance its visibility to the user.

An optional contact lens 66, which can be any suitable ophthalmic lens, can be used to help further focus the optical beam 6 into the patient's eye 68 while helping to stabilize eye position. The positioning and character of optical beam 6 and/or the scan pattern the beam 6 forms on the eye 68 may be further controlled by use of an input device such as a joystick, or any other appropriate user input device (e.g. GUI 304) to position the patient and/or the optical system.

The UF laser 4 and controller 300 can be set to target the surfaces of the targeted structures in the eye 68 and ensure that the beam 6 will be focused where appropriate and not unintentionally damage non-targeted tissue. Imaging modalities and techniques described herein, such as for example, Optical Coherence Tomography (OCT), Purkinje imaging, Scheimpflug imaging, or ultrasound may be used to determine the location and measure the thickness of the lens and lens capsule to provide greater precision to the laser focusing methods, including 2D and 3D patterning. Laser focusing may also be accomplished using one or more methods including direct observation of an aiming beam, Optical Coherence Tomography (OCT), Purkinje imaging, Scheimpflug imaging, ultrasound, or other known ophthalmic or medical imaging modalities and/or combinations thereof. In the embodiment of FIG. 1, an OCT device 100 is described, although other modalities are within the scope of the present invention. An OCT scan of the eye will provide information about the axial location of the anterior and posterior lens capsule, the boundaries of the cataract nucleus, as well as the depth of the anterior chamber. This information is then be loaded into the control electronics 300, and used to program and control the subsequent laser-assisted surgical procedure. The information may also be used to determine a wide variety of parameters related to the procedure such as, for example, the upper and lower axial limits of the focal planes used for cutting the lens capsule and segmentation of the lens cortex and nucleus, and the thickness of the lens capsule among others.

The OCT device 100 in FIG. 1 includes a broadband or a swept light source 102 that is split by a fiber coupler 104 into a reference arm 106 and a sample arm 110. The reference arm 106 includes a module 108 containing a reference reflection along with suitable dispersion and path length compensation. The sample arm 110 of the OCT device 100 has an output connector 112 that serves as an interface to the rest of the UF laser system. The return signals from both the reference and sample arms 106, 110 are then directed by coupler 104 to a detection device 128, which employs either time domain, frequency or single point detection techniques. In FIG. 1, a frequency domain technique is used with an OCT wavelength of 920 nm and bandwidth of 100 nm.

Exiting connector 112, the OCT beam 114 is collimated using lens 116. The size of the collimated beam 114 is determined by the focal length of lens 116. The size of the beam 114 is dictated by the desired NA at the focus in the eye and the magnification of the beam train leading to the eye 68. Generally, OCT beam 114 does not require as high an NA as the UF beam 6 in the focal plane and therefore the OCT beam 114 is smaller in diameter than the UF beam 6 at the beam combiner 34 location. Following collimating lens 116 is aperture 118 which further modifies the resultant NA of the OCT beam 114 at the eye. The diameter of aperture 118 is chosen to optimize OCT light incident on the target tissue and the strength of the return signal. Polarization control element 120, which may be active or dynamic, is used to compensate for polarization state changes which may be induced by individual differences in corneal birefringence, for example. Mirrors 122 & 124 are then used to direct the OCT beam 114 towards beam combiners 126 & 34. Mirrors 122 & 124 may be adjustable for alignment purposes and in particular for overlaying of OCT beam 114 to UF beam 6 subsequent to beam combiner 34. Similarly, beam combiner 126 is used to combine the OCT beam 114 with the aim beam 202 described below.

Once combined with the UF beam 6 subsequent to beam combiner 34, OCT beam 114 follows the same path as UF beam 6 through the rest of the system. In this way, OCT beam 114 is indicative of the location of UF beam 6. OCT beam 114 passes through the z-scan 40 and x-y scan 50 devices then the objective lens 58, contact lens 66 and on into the eye 68. Reflections and scatter off of structures within the eye provide return beams that retrace back through the optical system, into connector 112, through coupler 104, and to OCT detector 128. These return back reflections provide the OCT signals that are in turn interpreted by the system as to the location in X, Y Z of UF beam 6 focal location.

OCT device 100 works on the principle of measuring differences in optical path length between its reference and sample arms. Therefore, passing the OCT through z-adjust 40 does not extend the z-range of OCT system 100 because the optical path length does not change as a function of movement of 42. OCT system 100 has an inherent z-range that is related to the detection scheme, and in the case of frequency domain detection it is specifically related to the spectrometer and the location of the reference arm 106. In the case of OCT system 100 used in FIG. 1, the z-range is approximately 1-2 mm in an aqueous environment. Extending this range to at least 4 mm involves the adjustment of the path length of the reference arm within OCT system 100. Passing the OCT beam 114 in the sample arm through the z-scan of z-adjust 40 allows for optimization of the OCT signal strength. This is accomplished by focusing the OCT beam 114 onto the targeted structure while accommodating the extended optical path length by commensurately increasing the path within the reference arm 106 of OCT system 100.

Because of the fundamental differences in the OCT measurement with respect to the UF focus device due to influences such as immersion index, refraction, and aberration, both chromatic and monochromatic, care must be taken in analyzing the OCT signal with respect to the UF beam focal location. A calibration or registration procedure as a function of X, Y Z should be conducted in order to match the OCT signal information to the UF focus location and also to the relate to absolute dimensional quantities.

Observation of an aim beam may also be used to assist the user to directing the UF laser focus. Additionally, an aim beam visible to the unaided eye in lieu of the infrared OCT and UF beams can be helpful with alignment provided the aim beam accurately represents the infrared beam parameters. An aim subsystem 200 is employed in the configuration shown in FIG. 1. The aim beam 202 is generated by a an aim beam light source 201, such as a helium-neon laser operating at a wavelength of 633 nm. Alternatively a laser diode in the 630-650 nm range could be used. The advantage of using the helium neon 633 nm beam is its long coherence length, which would enable the use of the aim path as a laser unequal path interferometer (LUPI) to measure the optical quality of the beam train, for example.

Once the aim beam light source generates aim beam 202, the aim beam 202 is collimated using lens 204. The size of the collimated beam is determined by the focal length of lens 204. The size of the aim beam 202 is dictated by the desired NA at the focus in the eye and the magnification of the beam train leading to the eye 68. Generally, aim beam 202 should have close to the same NA as UF beam 6 in the focal plane and therefore aim beam 202 is of similar diameter to the UF beam at the beam combiner 34 location. Because the aim beam is meant to stand-in for the UF beam 6 during system alignment to the target tissue of the eye, much of the aim path mimics the UF path as described previously. The aim beam 202 proceeds through a half-wave plate 206 and linear polarizer 208. The polarization state of the aim beam 202 can be adjusted so that the desired amount of light passes through polarizer 208. Elements 206 & 208 therefore act as a variable attenuator for the aim beam 202. Additionally, the orientation of polarizer 208 determines the incident polarization state incident upon beam combiners 126 and 34, thereby fixing the polarization state and allowing for optimization of the beam combiners' throughput. Of course, if a semiconductor laser is used as aim beam light source 200, the drive current can be varied to adjust the optical power.

The aim beam 202 proceeds through a shutter 210 and aperture 212. The system controlled shutter 210 provides on/off control of the aim beam 202. The aperture 212 sets an outer useful diameter for the aim beam 202 and can be adjusted appropriately. A calibration procedure measuring the output of the aim beam 202 at the eye can be used to set the attenuation of aim beam 202 via control of polarizer 206.

The aim beam 202 next passes through a beam conditioning device 214. Beam parameters such as beam diameter, divergence, circularity, and astigmatism can be modified using one or more well known beaming conditioning optical elements. In the case of an aim beam 202 emerging from an optical fiber, the beam conditioning device 214 can simply include a beam expanding telescope with two optical elements 216 and 218 in order to achieve the intended beam size and collimation. The final factors used to determine the aim beam parameters such as degree of collimation are dictated by what is necessary to match the UF beam 6 and aim beam 202 at the location of the eye 68. Chromatic differences can be taken into account by appropriate adjustments of beam conditioning device 214. In addition, the optical system 214 is used to image aperture 212 to a desired location such as a conjugate location of aperture 14.

The aim beam 202 next reflects off of fold mirrors 222 & 220, which are preferably adjustable for alignment registration to UF beam 6 subsequent to beam combiner 34. The aim beam 202 is then incident upon beam combiner 126 where the aim beam 202 is combined with OCT beam 114. Beam combiner 126 reflects the aim beam 202 and transmits the OCT beam 114, which allows for efficient operation of the beam combining functions at both wavelength ranges. Alternatively, the transmit and reflect functions of beam combiner 126 can be reversed and the configuration inverted. Subsequent to beam combiner 126, aim beam 202 along with OCT beam 114 is combined with UF beam 6 by beam combiner 34.

A device for imaging the target tissue on or within the eye 68 is shown schematically in FIG. 1 as imaging system 71. Imaging system includes a camera 74 and an illumination light source 86 for creating an image of the target tissue. The imaging system 71 gathers images which may be used by the system controller 300 for providing pattern centering about or within a predefined structure. The illumination light source 86 for the viewing is generally broadband and incoherent. For example, light source 86 can include multiple LEDs as shown. The wavelength of the viewing light source 86 is preferably in the range of 700 nm to 750 nm, but can be anything which is accommodated by the beam combiner 56, which combines the viewing light with the beam path for UF beam 6 and aim beam 202 (beam combiner 56 reflects the viewing wavelengths while transmitting the OCT and UF wavelengths). The beam combiner 56 may partially transmit the aim wavelength so that the aim beam 202 can be visible to the viewing camera 74. Optional polarization element 84 in front of light source 86 can be a linear polarizer, a quarter wave plate, a half-wave plate or any combination, and is used to optimize signal. A false color image as generated by the near infrared wavelength is acceptable.

The illumination light from light source 86 is directed down towards the eye using the same objective lens 58 and contact lens 66 as the UF and aim beam 6, 202. The light reflected and scattered off of various structures in the eye 68 are collected by the same lenses 58 & 66 and directed back towards beam combiner 56. There, the return light is directed back into the viewing path via beam combiner and mirror 82, and on to camera 74. Camera 74 can be, for example but not limited to, any silicon based detector array of the appropriately sized format. Video lens 76 forms an image onto the camera's detector array while optical elements 80 & 78 provide polarization control and wavelength filtering respectively. Aperture or iris 81 provides control of imaging NA and therefore depth of focus and depth of field. A small aperture provides the advantage of large depth of field which aids in the patient docking procedure. Alternatively, the illumination and camera paths can be switched. Furthermore, aim light source 200 can be made to emit in the infrared which would not directly visible, but could be captured and displayed using imaging system 71.

Coarse adjust registration is usually needed so that when the contact lens 66 comes into contact with the cornea, the targeted structures are in the capture range of the X, Y scan of the system. Therefore a docking procedure is preferred, which preferably takes in account patient motion as the system approaches the contact condition (i.e. contact between the patient's eye 68 and the contact lens 66. The viewing system 71 is configured so that the depth of focus is large enough such that the patient's eye 68 and other salient features may be seen before the contact lens 66 makes contact with eye 68.

Preferably, a motion control system 70 is integrated into the overall control system 2, and may move the patient, the system 2 or elements thereof, or both, to achieve accurate and reliable contact between contact lens 66 and eye 68. Furthermore, a vacuum suction subsystem and flange may be incorporated into system 2, and used to stabilize eye 68. The alignment of eye 68 to system 2 via contact lens 66 may be accomplished while monitoring the output of imaging system 71, and performed manually or automatically by analyzing the images produced by imaging system 71 electronically by means of control electronics 300 via IO 302. Force and/or pressure sensor feedback may also be used to discern contact, as well as to initiate the vacuum subsystem.

Figure 2:
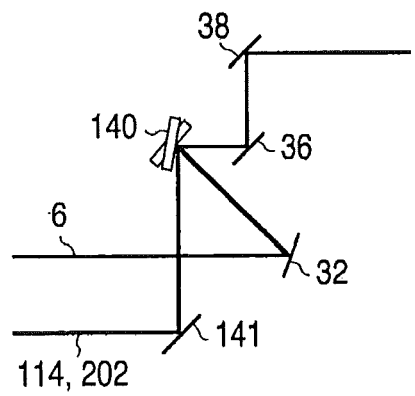
FIG. 2 is an optical diagram showing an alternative beam combining scheme.

An alternative beam combining configuration is shown in the alternate embodiment of FIG. 2. For example, the passive beam combiner 34 in FIG. 1 can be replaced with an active combiner 140 in FIG. 2. The active beam combiner 34 can be a moving or dynamically controlled element such as a galvanometric scanning mirror, as shown. Active combiner 140 changes it angular orientation in order to direct either the UF beam 6 or the combined aim and OCT beams 202,114 towards the scanner 50 and eventually eye 68 one at a time. The advantage of the active combining technique is that it avoids the difficulty of combining beams with similar wavelength ranges or polarization states using a passive beam combiner. This ability is traded off against the ability to have simultaneous beams in time and potentially less accuracy and precision due to positional tolerances of active beam combiner 140.

Figure 3:
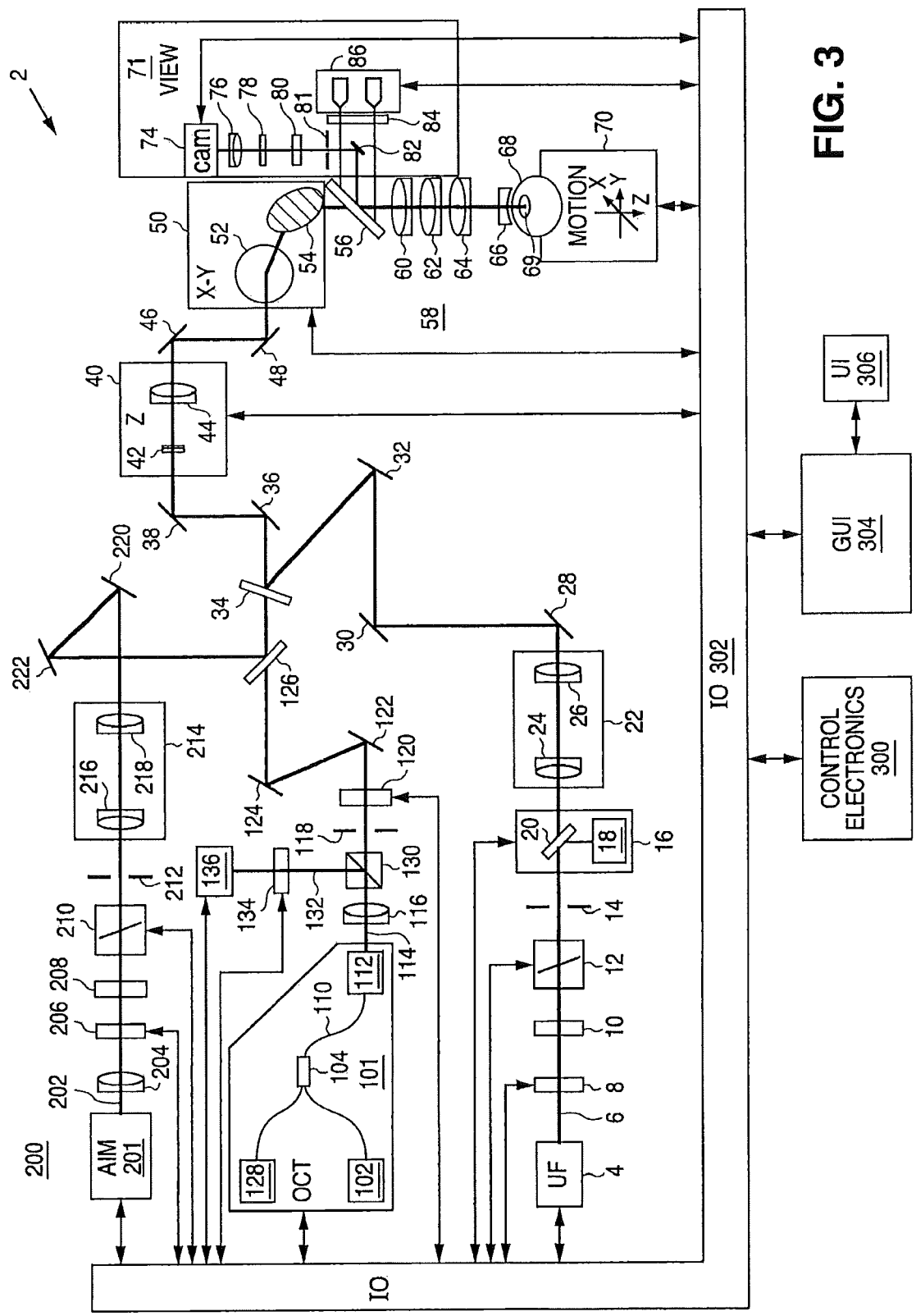
FIG. 3 is a schematic diagram of the optical beam scanning system with an alternative OCT configuration.

Another alternate embodiment is shown in FIG. 3 which is similar to that of FIG. 1 but utilizes an alternate approach to OCT 100. In FIG. 3, OCT 101 is the same as OCT 100 in FIG. 1, except that the reference arm 106 has been replaced with reference arm 132. This free-space OCT reference arm 132 is realized by including beam splitter 130 after lens 116. The reference beam 132 then proceeds through polarization controlling element 134 and then onto the reference return module 136. The reference return module 136 contains the appropriate dispersion and path length adjusting and compensating elements and generates an appropriate reference signal for interference with the sample signal. The sample arm of OCT 101 now originates subsequent to beam splitter 130. The potential advantages of this free space configuration include separate polarization control and maintenance of the reference and sample arms. The fiber based beam splitter 104 of OCT 101 can also be replaced by a fiber based circulator. Alternately, both OCT detector 128 and beam splitter 130 might be moved together as opposed to reference arm 136.

Figure 4:
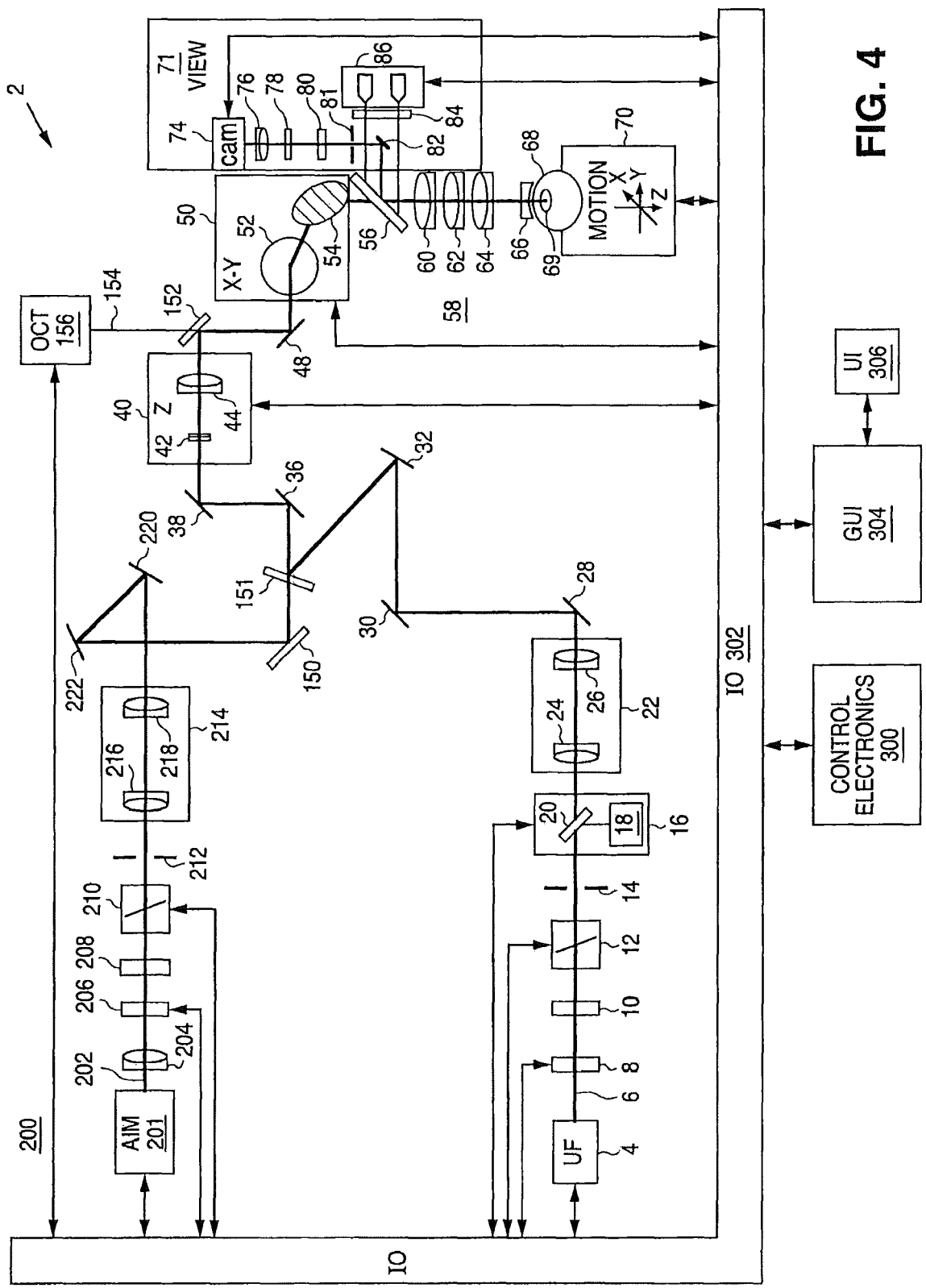
FIG. 4 is a schematic diagram of the optical beam scanning system with another alternative OCT combining scheme.

FIG. 4 shows another alternative embodiment for combining OCT beam 114 and UF beam 6. In FIG. 4, OCT 156 (which can include either of the configurations of OCT 100 or 101) is configured such that its OCT beam 154 is coupled to UF beam 6 after the z-scan 40 using beam combiner 152. In this way, OCT beam 154 avoids using the z-adjust. This allows the OCT 156 to possibly be folded into the beam more easily and shortening the path length for more stable operation. This OCT configuration is at the expense of an optimized signal return strength as discussed with respect to FIG. 1. There are many possibilities for the configuration of the OCT interferometer, including time and frequency domain approaches, single and dual beam methods, swept source, etc, as described in U.S. Pat. Nos. 5,748,898; 5,748,352; 5,459,570; 6,111,645; and 6,053,613 (which are incorporated herein by reference.)

Figure 5A:
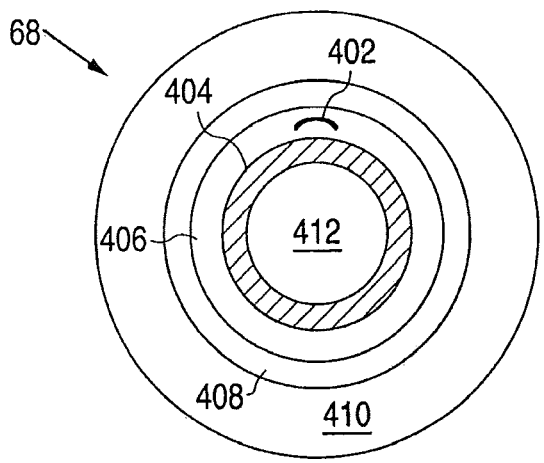
FIG. 5A is a top view of a patient's eye showing a cataract incision.
Figure 5B:
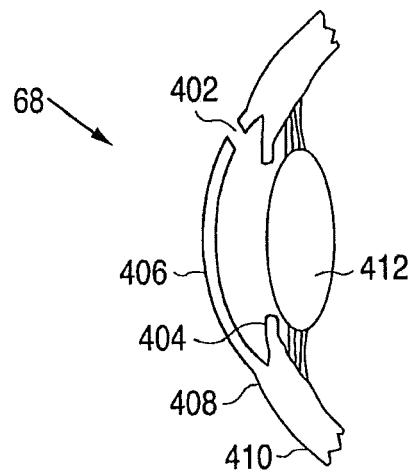
FIG. 5B is a side cross sectional view of a patient's eye showing the cataract incision.

The present invention provides for creating the incision to allow access for the lens removal instrumentation, typically referred to as the "cataract incision." This is shown as cataract incision 402 on the patient's eye 68 illustrated in FIGS. 5A & 5B. In these figures cataract incision 402 is made to eye 68 to provide access to crystalline lens 412 through cornea 406 while pupil 404 is dilated. The incision 402 is shown in cornea 406, but could be alternately placed in limbus 408 or sclera 410. The incision may be made with adjustable arcuate dimensions (both radius and extent), radial orientation and depth. A complete cut may not be desirable in all situations, such as in an unsterile field where opening the eye to the environment poses further risks of endophthalmitis, for example. In this case, the present invention may provide a cataract incision that only partially penetrates cornea 406, limbus 408 and/or sclera 410. The resident imaging apparati in system 2 may also provide input for planning the incision. For example, imaging system 71 and/or OCT 100 could identify the limbal boundary, and guide the incision to follow it along at a predetermined depth. Furthermore, surgeons often have difficulty in starting the incision at the correct location relative to limbus 410 when employing cold steel techniques, as well as keeping the knife straight to avoid incisions that ultimately penetrate both cornea 406 and sclera 410. Such angled incisions prove more likely to have torn edges and significantly higher risks of endophthalmitis.

The present invention may make use of the integrated OCT system 100 to discern limbus 408 and sclera 410 relative to cornea 406 by virtue of the large optical scattering differences between them. These can be directly imaged using OCT device 100, and the location of the transition (limbus 408) from clear (cornea 406) to scattering (sclera 410) can be determined and used by CPU 300 of system 2 to guide the placement of the laser-created incisions. The scanner position values corresponding to this transition define the location of limbus 408. Thus, once registered to each other, OCT 100 can guide the position of beam 6 relative to limbus 408. This same imaging approach may be used to discern the thickness of the tissue, as well. Thus, the depth of the incisions and their disposition within the tissue may be precisely defined. With that in mind, the choice of wavelength for OCT device 100 preferably accounts for the requirement of scleral measurement. Wavelengths in the range of 800-1400 nm are especially suited for this, as they are less scattered in tissue (and penetrate to depths of .about.1 mm) while not suffering from linear optical absorption by water or other tissue constituents that would otherwise diminish their performance.

Standard cataract incisions typically require .about.30.degree. of limbal angle as seen from directly above the eye. Such incisions have been shown to induce from 0-1.0 D of astigmatism, on average. Thus, achieving postoperative emmetropia can be made more difficult. To address astigmatism, the present invention may also produce Astigmatic Kerototomy (AK) incisions. Such incisions are routinely used to correct astigmatism by relaxing an asymmetrically shaped cornea along its steep axis. Similar to the cataract incision, such relaxing incisions (RIs) must be accurately placed along or nearby the limbus and are known as Limbal Relaxing Incisions (LRIs). Relaxing incisions, however, are only partially penetrating incisions. They should leave at least 200 .mu.m of tissue thickness in order to maintain its ongoing structural integrity. Similarly, Corneal Relaxing Incisions (CRIs) are incisions that are placed anterior to the limbus in the clear corneal tissue to serve the same clinical purpose of astigmatic correction. In addition to the specific clinical details, the circumferential orientation and angular extent are also influenced by the cataract incision. Thus, with the present invention, the RIs may be planned and executed in conjunction with the cataract incision to achieve a better visual correction than otherwise possible. To optimize the entire treatment, the cataract incision should not be placed at or near the steep axis of the cornea. If it is, only one RI is traditionally recommended. There are a variety of nomograms based upon empirical observations that are currently used by clinicians to prescribe the placement and extent of RIs. These include, but are not limited to, the Donnenfeld, Gills, Nichamin, and Koch nomograms.

Figure 6:
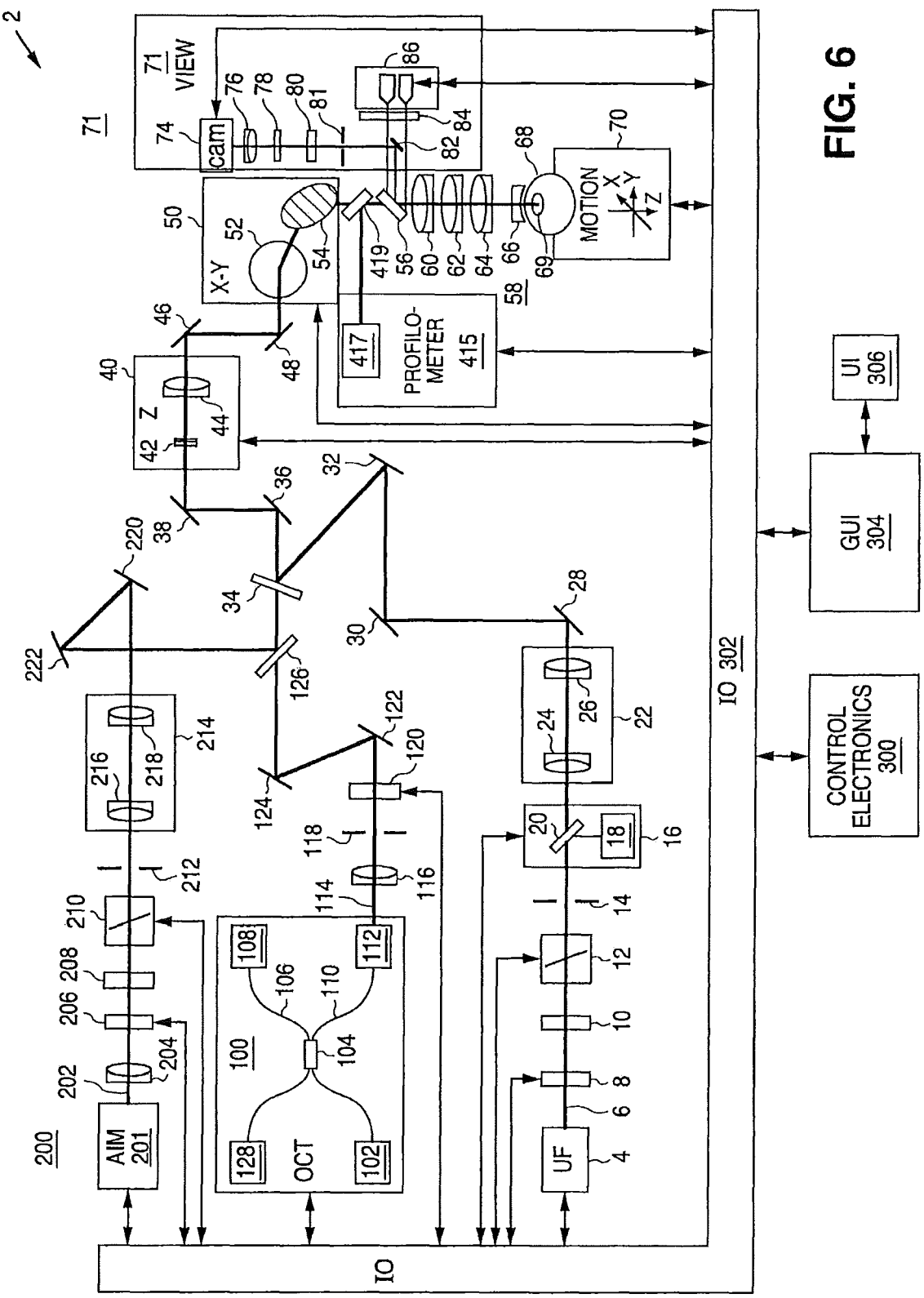
FIG. 6 is a schematic diagram of the optical beam scanning system with a profilometer subsystem.
Figure 9:
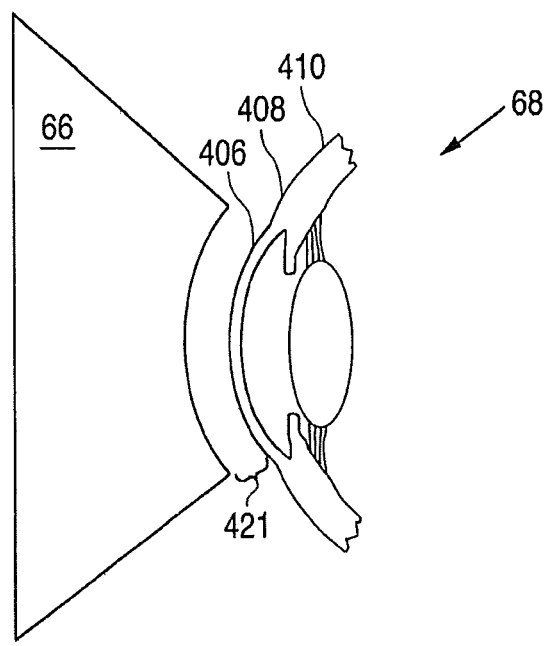
FIG. 9 is a side cross sectional view of a contact lens in proximity to a patient's eye.

FIG. 6 illustrates system 2 as shown in FIG. 1, but with a sub-system to characterize the astigmatism of the patient's cornea. Specifically, a profilometer 415 distal to X-Y scanner 50 is included to allow for a continuous unobstructed view of the cornea of patient's eye 68. Profilometer 415 and its sensor 417 are added to system 2 via beam combiner 419 and are connected as shown in FIG. 6 to the system controller 300 through input/output bus 302. As compared to the configuration described in FIG. 1, in this embodiment, contact lens 66 or its disposition relative to cornea 406 of eye 68 may have to be modified, or compensated for, to suit the profilometer's mode of operation. This is because profilometer 415 requires the cornea to be in its natural state, not forced into contact with a surface and possibly conforming to its shape, to accurately measure cornea 406 and provide data to system 2 for calculation and registration via input/output bus 302 and control electronics 300. Alternately, contact lens 66 may be removed from contact with the eye, and the diagnostic and therapeutic portions of system 2 made to traverse gap 421 to eye 68 as shown in FIG. 9. The change in relationship between eye 68 and system 2 made by removing contact lens 66 must then be accounted for in ranging and registration of beams 6, 114, and 202. The use of OCT 100 to discern the location and shape of cornea 406 is especially useful in this regard, as the reflection from cornea 406 will provide a very strong signal making registration straight forward.

In this embodiment, profilometer 415 may be used to prescribe an astigmatic keratotomy to correct the shape of a patient's cornea to diminish its astigmatism. The profilometer 415 may be a placido system, triangulation system, laser displacement sensor, interferometer, or other such device, which measures the corneal topography also known as the surface profile or the surface sag (i.e. sagitta) of the cornea as a function of the transverse dimension to some defined axis. This axis is typically the visual axis of the eye but can also be the optical axis of the cornea. Alternately, profilometer 415 may be replaced by a wavefront sensor to more fully optically characterize the patient's eye. A wavefront sensing system measures the aberration of the eye's optical system. A common technique for accomplishing this task is a Shack-Hartmann wavefront sensor, which measures the shape of the wavefronts of light (surfaces of constant phase) that exit the eye's pupil. If the eye were a perfect optical system, these wavefronts would be perfectly flat. Since the eye is not perfect, the wavefronts are not flat and have irregular curved shapes. A Shack-Hartmann sensor divides up the incoming beam and its overall wavefront into sub-beams, dividing up the wavefront into separate facets, each focused by a microlens onto a subarray of detection pixels. Depending upon where the focal spot from each facet strikes its subarray of pixels, it is then possible to determine the local wavefront inclination (or tilt). Subsequent analysis of all facets together leads to determination of the overall wavefront form. These deviations from the perfectly overall flat wavefront are indicative of the localized corrections that can be made in the corneal surface. The measurements of the wavefront sensor may be used by controller 300 to automatically prescribe an astigmatic keratotomy via predictive algorithms resident in the system, as mentioned above.

Figure 7:
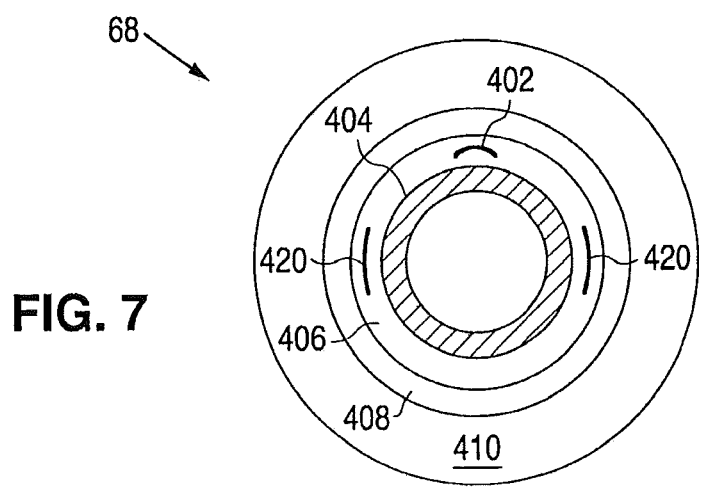
FIG. 7 is a top view of a patient's eye showing corneal relaxing incisions.

FIG. 7 shows a possible configuration of such an astigmatic keratotomy. In this example, eye 68 is shown and a set of relaxing incisions RI 420 are made at locations within the area of the cornea 406. Likewise, as is known in the art, such relaxing incisions may be made in the limbus 408, or sclera 410. Astigmatism is present when the cornea is not spherical; that is, it is steeper in one meridian than other (orthogonal) meridian. Determining the nature of the corneal shape is important, whether the astigmatism is "with-the-rule," "against-the-rule," or oblique. In "with-the-rule" astigmatism, the vertical meridian is steeper than the horizontal meridian; in "against-the-rule" astigmatism, the horizontal meridian is steeper than the vertical meridian. Limbal relaxing incisions (LRIs) are a modification of astigmatic keratotomy (AK), a procedure to treat astigmatism. LRIs are placed on the far peripheral aspect of the cornea (the limbus), resulting in a more rounded cornea. Astigmatism is reduced, and uncorrected vision is improved. LRIs can correct astigmatism up to 8 diopters (D); however, the use of LRIs is presently routinely reserved for corrections of 0.5-4 D of astigmatism. Although LRIs are a weaker corrective procedure compared to corneal relaxing incisions (CRIs), LRIs produce less postoperative glare and less patient discomfort. In addition, these incisions heal faster. Unlike CRIs, making the incision at the limbus preserves the perfect optical qualities of the cornea. LRIs are also a more forgiving procedure, and surgeons often get excellent results, even with early cases.

The desired length, number, and depth of relaxing incisions 420 can be determined using nomograms. A starting point nomogram can titrate surgery by length and number of LRIs. However, the length and placement can vary based on topography and other factors. The goal is to reduce cylindrical optical power and to absolutely avoid overcorrecting with-the-rule astigmatism, because against-the-rule astigmatism should be minimized. Relaxing incisions formed in the sclera, limbus, or cornea are generally used for cases of with-the-rule astigmatism and low against-the-rule astigmatism. When using the relaxing incision in conjunction with against-the-rule astigmatism, the LRI can be moved slightly into the cornea, or, alternatively, the LRI could be placed opposite another relaxing incision in the sclera, limbus or cornea. For patients who have with-the-rule astigmatism or oblique astigmatism, the relaxing incision is made temporally, and the LRIs are placed at the steep axis. The placement of the LRI should be customized to the topography of the cornea. In cases of asymmetric astigmatism, the LRI in the steepest axis can be elongated slightly and then shortened the same amount in the flatter of the 2 steep axes. Paired LRIs do not have to be made in the same meridian. Patients with low (<1.5 D) against-the-rule astigmatism receive only a single LRI in the steep meridian, placed opposite to the cataract incision. However, if astigmatism is greater than 1.5 D, a pair of LRIs should be used. In against-the-rule astigmatism cases, one pair of LRIs may be incorporated into the cataract incision. The length of the LRI is not affected by the presence of the cataract incision. This is difficult to perform precisely with present methods. In low with-the-rule astigmatism cases, a single 6-mm LRI (0.6 mm in depth) is made at 90.degree. The LRI can be independent of the cataract incision in with-the-rule astigmatism cases (if the cataract incision is temporal and the LRI is superior).

Furthermore, unlike traditional cold steel surgical approaches to creating incisions that must start at the outside and cut inwards, using a light source for making these incisions allows for RI 420 to be made from the inside out and thus better preserve the structural integrity of the tissue and limit the risk of tearing and infection. Moreover, the cataract incision 402 and the relaxation incision(s) 420 can be made automatically using the imaging and scanning features of system 2. A pair of treatment patterns can be generated that forms incisions 402 and 420, thus providing more accurate control over the absolute and relative positioning of these incisions. The pair of treatment patterns can be applied sequentially, or simultaneously (i.e. the pair of treatment patterns can be combined into a single treatment pattern that forms both types of incisions). For proper alignment of the treatment beam pattern, an aiming beam and/or pattern from system 2 can be first projected onto the target tissue with visible light indicating where the treatment pattern(s) will be projected. This allows the surgeon to adjust and confirm the size, location and shape of the treatment pattern(s) before their actual application. Thereafter, the two or three dimensional treatment pattern(s) can be rapidly applied to the target tissue using the scanning capabilities of system 2.

Figure 8:
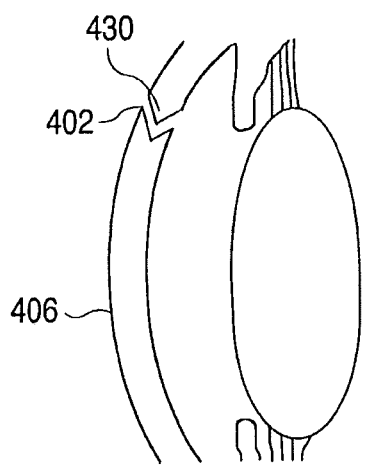
FIG. 8 is a side cross sectional view of a patient's eye showing an incision with a specialized geometry.

Specialized scan patterns for creating alternate geometries for cataract incisions 402 that are not achievable using conventional techniques are also possible. An example is illustrated in FIG. 8. A cross-sectional view of an alternate geometry for cataract incision 402 is shown to have a bevel feature 430. Bevel feature 430 may be useful for wound healing, sealing, or locking. Such 3-dimensional cataract incisions 402 can be achieved accurately and quickly utilizing the 3-dimensional scanning ability of system 2. Although a beveled incision is shown, many such geometries are enabled using the present invention, and within its scope. As before, the incision 402 is shown in cornea 406, but could be alternately placed in limbus 408 or sclera 410.

For large fields as when incisions are made in the outer most regions such as the limbus or sclera, a specialized contact lens can be used. This contact lens could be in the form of a gonioscopic mirror or lens. The lens does not need to be diametrically symmetric. Just one portion of the lens can be extended to reach the outer regions of the eye such as the limbus 408 and sclera 410. Any targeted location can be reached by the proper rotation of the specialized lens.

It is to be understood that the present invention is not limited to the embodiment(s) described above and illustrated herein, but encompasses any and all variations falling within the scope of the appended claims. For example, references to the present invention herein are not intended to limit the scope of any claim or claim term, but instead merely make reference to one or more features that may be covered by one or more of the claims. All the optical elements downstream of scanner 50 shown in FIGS. 1, 3 and 4 form a delivery system of optical elements for delivering the beam 6, 114 and 202 to the target tissue. Conceivably, depending on the desired features of the system, some or even most of the depicted optical elements could be omitted in a delivery system that still reliably delivers the scanned beams to the target tissue.

What is claimed is:

1. A scanning system for treating target tissue in a patient's eye, comprising:
 a) an ultrafast laser source configured to deliver a laser beam comprising a plurality of laser pulses;
 b) an Optical Coherence Tomography (OCT) device configured to generate signals which may be used to create an image of the cornea and limbus of the eye of the patient;
 c) a scanner configured to focus and direct the laser beam in a pattern within the cornea or limbus to create incisions therein; and
 d) a controller operatively coupled to the laser source and scanner programmed to determine a treatment pattern based upon the signals from the OCT device, the treatment pattern forming a cataract incision in the cornea that provides access for lens removal instrumentation to a crystalline lens of the patient's eye and one or more relaxation incisions in the cornea or limbus, wherein the cataract incision has an arcuate extent of less than 360 degrees in a top view, wherein the cataract incision includes a bevel shape in a cross-sectional view, the bevel shape including a first segment and a second segment which intersect each other at an angle, the cataract incision being entirely located in the cornea and intersecting both an anterior surface and a posterior surface of the cornea, and to control the scanner to scan the position of the laser beam in the treatment pattern.

2. The system of claim 1, wherein the controller is programmed to operate the laser source and scanner such that at least one of the incisions only partially extends through the target tissue.

3. The system of claim 1, further comprising: a profilometer for measuring a surface profile of a surface of the cornea of the patient's eye, wherein the controller is programmed to determine the treatment pattern in response to the measured surface profile.

4. The system of claim 1, wherein the OCT device is configured to measure scattering properties from different locations on the patient's eye, wherein the controller is programmed to determine the treatment pattern in response to the scattering properties.

5. The system of claim 1, wherein the controller is programmed to operate the laser source and scanner to create incisions within the tissue at a depth based upon the signals from the OCT device.

6. The system of claim 1, wherein the scanner comprises a Z-scan device operable to move a focus position of the laser beam along a z-axis and a X-Y scan device operable to move the focus position of the laser beam laterally relative to the z-axis.

7. The system of claim 6, wherein the OCT device produces an OCT beam that passes through the Z-scan device and the X-Y scan device.

8. The system of claim 1, wherein the ultrafast laser source is configured to deliver a laser beam having a wavelength between 1010 nm to 1100 nm.

9. The system of claim 1, wherein the ultrafast laser source is configured to deliver laser pulses having pulse lengths of 100 fs to 10000 fs.

10. The system of claim 1, wherein the ultrafast laser source is configured to deliver a plurality of laser pulses having a pulse repetition frequency of 10 kHz to 250 kHz.

11. The system of claim 1, wherein the OCT device comprises an OCT light source configured to generate a light beam having wavelengths of 800 nm to 1400 nm.

12. The system of claim 1, wherein the OCT device comprises a broadband OCT light source.

13. The system of claim 1, wherein the OCT device is a frequency domain OCT device.

14. The system of claim 13, wherein the frequency domain OCT device comprises a swept light source.

15. The system of claim 1, further comprising a wavefront sensing system configured to measure the optical aberration of the eye.

16. The system of claim 15, wherein the wavefront sensing system comprises a Shack-Hartmann wavefront sensor configured to measure a shape of a wavefront of light that exits the eye's pupil.

17. The system of claim 16, wherein a correction to the shape of the cornea is made based on the shape of the wavefront.

\* \* \* \* \*

(12) INTER PARTES REVIEW CERTIFICATE (3108th)

United States Patent
Culbertson et al.

(10) Number: US 10,709,548 K1
(45) Certificate Issued: Apr. 28, 2023

(54) METHOD AND APPARATUS FOR CREATING OCULAR SURGICAL AND RELAXING INCISIONS

(71) Applicants: William Culbertson; David Angeley; George Marcellino; Dan E. Andersen

(72) Inventors: William Culbertson; David Angeley; George Marcellino; Dan E. Andersen

(73) Assignee: OPTIMEDICA CORPORATION

Trial Number:

IPR2021-00849 filed Apr. 26, 2021

Inter Partes Review Certificate for:

Patent No.: 10,709,548
Issued: Jul. 14, 2020
Appl. No.: 14/668,696
Filed: Mar. 25, 2015

The results of IPR2021-00849 are reflected in this inter partes review certificate under 35 U.S.C. 318(b).

INTER PARTES REVIEW CERTIFICATE
U.S. Patent 10,709,548 K1
Trial No. IPR2021-00849
Certificate Issued Apr. 28, 2023

AS A RESULT OF THE INTER PARTES REVIEW PROCEEDING, IT HAS BEEN DETERMINED THAT:

Claims 1-14 are cancelled.

\* \* \* \* \*